US009326829B2

(12) United States Patent
Kojima et al.

(10) Patent No.: US 9,326,829 B2
(45) Date of Patent: May 3, 2016

(54) CAPSULE FOR TOOTH RESTORATIVE MATERIAL

(75) Inventors: Shinichi Kojima, Itabashi-ku (JP);
Masayuki Takahashi, Itabashi-ku (JP);
Tomohiro Uchida, Inashiki-gun (JP)

(73) Assignee: GC Corporation, Tokyo (JP)

( * ) Notice: Subject to any disclaimer, the term of this patent is extended or adjusted under 35 U.S.C. 154(b) by 996 days.

(21) Appl. No.: 12/839,722

(22) Filed: Jul. 20, 2010

(65) Prior Publication Data
US 2011/0027751 A1 Feb. 3, 2011

(30) Foreign Application Priority Data
Jul. 30, 2009 (JP) .................................. 2009-177853

(51) Int. Cl.
A61C 5/04 (2006.01)
A61C 5/06 (2006.01)

(52) U.S. Cl.
CPC ............... *A61C 5/062* (2013.01); *A61C 5/064* (2013.01)

(58) Field of Classification Search
CPC .............................. A61C 5/062; A61C 5/064
USPC ................ 433/80, 39, 89–90, 155, 225, 227; 604/414–416
See application file for complete search history.

(56) References Cited

U.S. PATENT DOCUMENTS

| 5,026,283 A | 6/1991 | Osanai et al. |
| 5,240,397 A * | 8/1993 | Fay et al. ..................... 425/145 |
| 6,386,872 B1 * | 5/2002 | Mukasa et al. ................ 433/90 |
| 6,869,284 B2 * | 3/2005 | Aoyagi et al. ................ 433/90 |

FOREIGN PATENT DOCUMENTS

| EP | 1 219 262 A1 | 7/2002 |
| JP | 3-81384 B2 | 12/1991 |
| JP | 08-131459 A | 5/1996 |
| JP | 2000-246754 A | 9/2000 |
| JP | 3630738 B2 | 3/2005 |
| JP | 4073571 B2 | 4/2008 |

OTHER PUBLICATIONS

Extended European Search Report issued Nov. 24, 2010, in Patent Appplication No. 10007623.1.

* cited by examiner

*Primary Examiner* — Cris L Rodriguez
*Assistant Examiner* — Mirayda A Aponte
(74) *Attorney, Agent, or Firm* — Oblon, McClelland, Maier & Neustadt, L.L.P.

(57) ABSTRACT

To prevent a bursting sound generated when a mixed and kneaded material obtained by mixing and kneading predetermined amounts of a powder component and a liquid component in a capsule for a tooth restorative material is administrated to a position to be restored in a patient's tooth, the capsule is structured such that a protrusion portion (4c) having its inner end positioned slightly inside an outer periphery of a circular hole of a first opening forming portion (1b) is provided on a rear end portion of a nozzle (4) in such a manner as to be positioned at a position which is in the vicinity of the first opening forming portion (1b) to form the circular hole for an outlet of a mixed and kneaded material (C) of a powder component storing cup (1) and is away from at least a hinge portion of the circular hole.

1 Claim, 2 Drawing Sheets

CAPSULE FOR TOOTH RESTORATIVE MATERIAL

BACKGROUND OF THE INVENTION

1. Field of the Invention

The present invention relates to a capsule for a tooth restorative material which can be administered to a position to be restored of a patient immediately after mixing and kneading a dental restorative material constructed by two components of a powder component and a liquid component, in a filling use, a connection use, a backing use and the other intended uses for restoring the tooth in a dental treatment field, and does not generate any bursting sound at a time of starting the administration.

2. Description of the Conventional Art

Generally, the tooth restorative material is used for restoring the tooth, and, as the tooth restorative material, there has been generally used a two-component type material including a powder component and a liquid component which are reacted by mixing and kneading. Conventionally, this two-component type tooth restorative material is used by weighing the powder component and the liquid component on a scale appropriately in each case. However, in recent years, for the purpose of omitting a weighing work of the powder component and the liquid component and a work for storing the tooth restorative material after mixing and kneading in a syringe for administering it at a position to be restored, there has been developed a capsule for the tooth restorative material which stores fixed amounts of a powder component and a liquid component which have been previously weighed respectively in an isolated state, where the isolated state is cancelled at a desired time so as to be mechanically mixed and kneaded by a mixer or the like, and the mixed and kneaded material is directly extruded to administer to a position to be restored such as a cavity or the like of the tooth via a nozzle. (refer, for example, to Japanese Patent Publication No. 3-81384).

As the capsule for the tooth restorative material mentioned above, there has been used a structure in which a liquid component is stored in a bag made of a raw material obtained by laminating a resin film on an aluminum foil so as to be arranged in a state of staying with a powder component, and is reacted with the powder component by pushing and breaking the bag at a time of being used, however, there is a defect that the liquid component flowing out of the bag broken at a time of use mixes into the powder component in a state of dissolving the aluminum foil of the broken surface of the bag in the case that the liquid component is acid, and a remaining piece of the broken portion of the bag mixes into the mixed material of the powder component and the liquid component.

In order to dissolve the defect mentioned above, the applicant of the present invention has previously proposed a capsule for a tooth restorative material in which a liquid component is stored in an isolated manner in a different section from a powder component without being put into a bag, and is mixed with the powder component by pushing the liquid component into the powder component side as well as pushing and breaking a partition wall of a liquid component storing cup at a time of use, and the mixed material is administered by pushing and breaking the partition wall communicating with a nozzle (refer, for example, to Japanese Patent No. 3630738).

FIG. 6 is an explanatory sectional view showing an example of the capsule for the tooth restorative material described in Japanese Patent No. 3630738. This capsule for the tooth restorative material is constructed by a powder component storing cup 1 which is formed in a cylinder shape, has a mixing comparted chamber 1a in which a powder component A is stored, is provided with a first opening forming portion 1b to form a circular hole for an outlet of a mixed and kneaded material of the powder component A and a liquid component B on a center axis of a front end portion thereof, is provided with an applier engagement groove 1d in an outer peripheral side surface near a rear end portion, and is integrally formed by injection molding of a thermoplastic synthetic resin, a liquid component storing cup 2 which stores the liquid component B, is provided with a second opening forming portion 2b to form a circular hole for an outlet of the liquid component B on a center axis of a front end portion, is fitted into the mixing comparted chamber 1a of the powder component storing cup 1, is provided with a convex stopper 2c for preventing easily slipping into the mixing comparted chamber 1a of the powder component storing cup 1 on an outer side surface in the vicinity of a rear end portion, and is integrally formed by injection molding of a thermoplastic synthetic resin, a plunger 3 which has a rod-like projection 3a having a planar peak portion for pushing and breaking the opening forming portions 2b and 1b at a front end, is fitted into the liquid component storing cup 2, and is integrally formed by injection molding of a thermoplastic synthetic resin, a cap 5 which has a nozzle engagement port on a center axis of a front end portion, is screwed with the powder component storing cup 1 at a rear portion inner peripheral side surface thereof, and is integrally formed by injection molding of a thermoplastic synthetic resin, and a nozzle 4 which is formed in a shape capable of engaging with an outer surface of the front end portion 1c of the powder component storing cup 1 at a rear end portion 4b thereof, is fixed to the powder component storing cup 1 by the cap 5, and is integrally formed by injection molding of a thermoplastic synthetic resin.

In order to use the capsule for the tooth restorative material as mentioned above, the circular hole is opened by first pressing the plunger 3 fitted into the rear end side of the liquid component storing cup 2 which is fitted into the rear end side of the mixing comparted chamber 1a of the powder component storing cup 1 until it stops by a finger, thereby pushing and breaking the second opening forming portion 2b at the front end side of the liquid component storing cup 2 by the planer peak portion of the rod-like projection 3a of the plunger 3, and the liquid component B is completely pressed into the mixing comparted chamber 1a of the powder component storing cup 1 in which the powder component A is stored, through the opened circular hole.

Accordingly, after both the components A and B are mixed and kneaded by installing the capsule for the tooth restorative material in which the liquid component B is completely pressed into the mixing comparted chamber 1a in which the powder component A is stored, to a mixer (not shown), the plunger 3 integrated with the liquid component storing cup 2 is moved forward on the basis of pressing force of an independently provided applier (not shown) by engaging a pawl of the applier with the applier engagement groove 1d provided in the rear end portion of the powder component storing cup 1. On the basis of this operation, the first opening forming portion 1b in the front end portion of the powder component storing cup 1 is pushed and broken by the planer peak portion of the rod-like projection 3a of the plunger 3, the circular hole is opened, and the mixed and kneaded material flows into the nozzle 4 through this hole so as to be administered to the portion to be restored in the tooth.

The second opening forming portion 2b to form the circular hole on the center axis of the front end portion of the liquid component storing cup 2, and the first opening forming portion 1b to form the circular hole on the center axis of the front end portion of the powder component storing cup 1 are easily pushed and broken by the planer peak portion of the rod-like projection 3a of the plunger 3 so as to respectively open the circular holes. Then, in order to prevent wholes of the pushed and broken opening forming portions 2b and 1b from being separated from the liquid component storing cup 2 and the powder component storing cup 1 so as to mix into the mixing comparted chamber 1a of the powder component storing cup 1 and the nozzle 4, a thick portion for giving strength is provided at a part of a locally weak portion having a circular shape so that the opening forming portion is pushed and broken in a state in which one end is coupled as if hinged to each of the storing cups 2 and 1 like as a door. Further, it is necessary to have enough strength to prevent the liquid component B stored in the inner portion in an unused storage state from leaking out to the mixing comparted chamber 1a of the powder component storing cup 1 and the nozzle 4.

Accordingly, the applicant of the present invention has found that the opening forming portions 2c and 1c can be easily and securely formed by applying a punch having a thermal welding blade or a cutting blade formed in a shape coinciding with the shape of the portion to be broken to one surface at a position corresponding to the portion to be broken at least around the partition wall portion to be pushed and broken until its cutting edge comes to a depth corresponding to a predetermined thickness of the portion to be broken around the partition wall portion to be pushed and broken, in a state in which a dolly block is brought into contact with the other surface, at a time of integrally forming the opening forming portions 2b and 1b which can form the circular holes which are easily pushed and broken, in the front end portions of the liquid component storing cup 2 and the powder component storing cup 1, by injection molding of the thermoplastic synthetic resin (refer, for example, to Japanese Patent No. 4073571).

If the circular hole is opened by using the capsule for the tooth restorative material having the structure described in Japanese Patent No. 3630738 in which the opening forming portions 2b and 1b are formed in accordance with the method of Japanese Patent No. 4073571, installing the capsule in which the liquid component B is completely pressed to the mixing comparted chamber 1a storing the powder component A to the mixer so as to mix and knead both the components A and B, thereafter engaging the pawl of the independently provided applier with the applier engagement groove 1d provided in the rear end portion of the powder component storing cup 1, moving forward the plunger 3 integrated with the liquid component storing cup 2 on the basis of pressing force of the applier, and pushing and breaking the first opening forming portion 1b in the front end portion of the powder component storing cup 1 by the planer peak portion of the rod-like projection 3a of the plunger 3, the circular hole is opened in a breath in a state in which air existing together with the mixed and kneaded material of both the components A and B is compressed within the mixing comparted chamber 1a of the powder component storing cup 1. Accordingly, there is a defect that the bursting sound is generated.

SUMMARY OF THE INVENTION

Problem to be Solved by the Invention

An object of the present invention is to provide a capsule for a tooth restorative material which is prevented from occurrence of a phenomenon that a bursting sound is generated, when a partition wall portion to be pushed and broken in a powder component storing cup, which is integrally formed by injection molding of a thermoplastic synthetic resin, is pushed and broken in a breath, in a capsule structured such that two kinds of reactive materials constructed by fixed amounts of a powder component and a liquid component, which are previously weighed on a scale respectively, are stored in an isolated state, and are mixed by pushing and breaking a partition wall between these two kinds of reactive materials at a time of use and pressing the liquid component to the powder component side so as to mix.

Means for Solving the Problem

The inventors of the present invention has completed the present invention by finding the following matter, as a result of devoting themselves to making a study for solving the object mentioned above. In accordance with the present invention, there is provided a capsule for a tooth restorative material for directly administering a mixed and kneaded material, which is obtained by mixing and kneading the tooth restorative material constructed by two components of previously weighed fixed amounts of a powder component and a liquid component in an inner portion, to a position to be restored in a tooth of a patient, the capsule comprising:

a powder component storing cup having a mixing comparted chamber in which the powder component is stored, formed in a cylinder shape, provided with a first opening forming portion to form a circular hole for an outlet of the mixed and kneaded material on a center axis of a front end portion thereof, provided with an applier engagement groove in an outer peripheral side surface near a rear end portion, and integrally formed by injection molding of a thermoplastic synthetic resin;

a liquid component storing cup having a liquid component storing chamber in which the liquid component is stored in an inner portion, provided with a second opening forming portion to form a circular hole for an outlet of a liquid component on a center axis of a front end portion thereof, fitted into the cylinder-shaped portion forming the mixing comparted chamber of the powder component storing cup, provided with a convex stopper having such a magnitude as to prevent easily slipping into the powder component storing cup at a time of pushing and breaking the second opening forming portion so as to form the circular hole for the outlet of the liquid component and not to inhibit entering into the powder component storing cup in the case that great force is applied on an outer side surface in the vicinity of the rear end portion, and integrally formed by injection molding of a thermoplastic synthetic resin;

a plunger having a rod-like projection including a planer peak portion for pushing and breaking the second opening forming portion of the liquid component storing cup and the first opening forming portion of the powder component storing cup, fitted into the cylinder-shaped portion within the liquid component storing cup, and integrally formed by injection molding of a thermoplastic synthetic resin; and a nozzle having its rear end portion formed in a shape corresponding to the front end portion of the powder component storing cup, fixed to the front end portion of the powder component storing cup, and integrally formed by injection molding of a thermoplastic synthetic resin, wherein a protrusion portion having its inner end positioned slightly inside an outer periphery of the circular hole of the first opening forming portion is provided on the rear end portion of the nozzle in such a manner as to be positioned at a position which is in the vicinity of the first opening forming portion to form the circular hole for the outlet of the mixed and kneaded material of the powder component storing cup and is away from at least a hinge portion of the circular hole. In accordance with this structure, since the protrusion portion obstructs the matter that the first opening forming portion of the powder component storing cup is pushed and broken in a breath, it is possible to prevent the occurrence of the phenomenon that the bursting sound is generated when the first opening forming portion of the powder component storing cup is pushed and broken in a breath.

In other words, in accordance with the present invention, there is provided a capsule for a tooth restorative material for directly administering a mixed and kneaded material, which is obtained by mixing and kneading the tooth restorative material constructed by two components of previously weighed fixed amounts of a powder component and a liquid component in an inner portion, to a position to be restored in a tooth of a patient, the capsule comprising:

a powder component storing cup having a mixing comparted chamber in which the powder component is stored, formed in a cylinder shape, provided with a first opening forming portion to form a circular hole for an outlet of the mixed and kneaded material of the powder component and the liquid component on a center axis of a front end portion thereof, provided with an applier engagement groove in an outer peripheral side surface near a rear end portion, and integrally formed by injection molding of a thermoplastic synthetic resin;

a liquid component storing cup in which the liquid component is stored and which is provided with a second opening forming portion to form a circular hole for an outlet of the liquid component on a center axis of a front end portion thereof, fitted into the mixing comparted chamber of the powder component storing cup, provided with a convex stopper for prevention of easily slipping into the mixing comparted chamber of the powder component storing cup on an outer side surface in the vicinity of the rear end portion, and integrally formed by injection molding of a thermoplastic synthetic resin;

a plunger having a rod-like projection including a planer peak portion for pushing and breaking both the opening forming portions, fitted to the liquid component storing cup, and integrally formed by injection molding of a thermoplastic synthetic resin; and a nozzle having its rear end portion formed in a shape corresponding to an outer surface of the front end portion of the powder component storing cup, fixed to the powder component storing cup, and integrally formed by injection molding of a thermoplastic synthetic resin, wherein a protrusion portion having its inner end positioned slightly inside an outer periphery of the circular hole of the first opening forming portion is provided on the rear end portion of the nozzle in such a manner as to be positioned at a position which is in the vicinity of the first opening forming portion to form the circular hole for the outlet of the mixed and kneaded material of the powder component storing cup and is away from at least a hinge portion of the circular hole.

Effect of the Invention

In the capsule for the tooth restorative material in accordance with the present invention, since the protrusion portion having its inner end positioned slightly inside the outer periphery of the circular hole of the first opening forming portion is provided on the rear end portion of the nozzle in such a manner as to be positioned at the nozzle side which is in the vicinity of the first opening forming portion to form the circular hole for the outlet of the mixed and kneaded material of the powder component storing cup and is away from at least the hinge portion of the circular hole, the protrusion portion obstructs the first opening forming portion of the powder component storing cup to be pushed and broken in a breath. Accordingly, it is possible to prevent the occurrence of the phenomenon that the first opening forming portion of the powder component storing cup is pushed and broken in a breath and the bursting sound is thereby generated.

BRIEF EXPLANATION OF DRAWINGS

A description will be in detail given below of an embodiment of a capsule for a tooth restorative material in accordance with the present invention with reference to the accompanying drawings.

DETAILED DESCRIPTION OF PREFERRED EMBODIMENT

Figure 1:
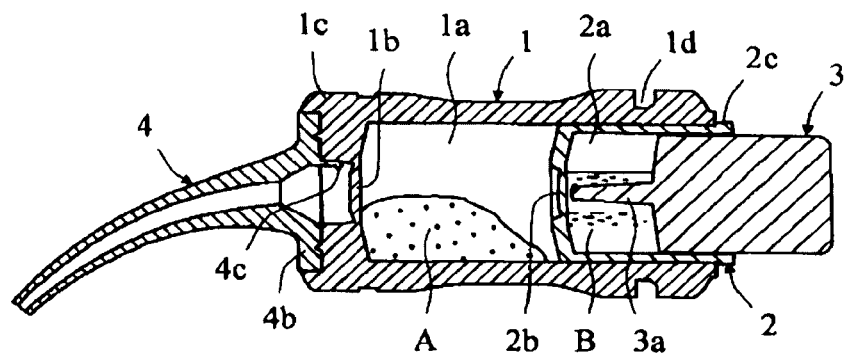
FIG. 1 is an explanatory side sectional view of an embodiment of a capsule for a tooth restorative material in accordance with the present invention.

In the drawings, reference numeral 1 denotes a powder component storing cup integrally formed by injection molding of a thermoplastic synthetic resin, made of a synthetic resin and formed in a cylinder shape. The powder component storing cup is provided with a mixing comparted chamber 1*a* in order to previously store a previously weighed fixed amount of powder component A in its inner portion, and to mix and knead the powder component A and a liquid component B at a time when the liquid component B flows therein, is provided with a first opening forming portion 1*b* to form a circular hole for an outlet of a mixed and kneaded material C obtained by mixing and kneading the powder component A and the liquid component B on a center axis of a front end portion 1*c* thereof, and has a shape corresponding to a nozzle 4 mentioned below at an outer surface of a front end portion, so that the nozzle 4 mentioned below is fixed. In this case, the powder component storing cup 1 is provided with an applier engagement groove 1*d* in an outer peripheral side surface near a rear end portion, and is preferably constructed by a resin which does not deteriorate a characteristic of the powder component A within the mixing comparted chamber 1*a*.

Reference numeral 2 denotes a liquid component storing cup having a liquid component storing chamber 2*a* which is integrally formed in a cylinder shape by injection molding of a thermoplastic synthetic resin, is made of a synthetic resin, and stores a previously weighed fixed amount of liquid component B in an inner portion thereof. The liquid component storing cup is provided with a second opening forming portion 2*b* to form a circular hole for an outlet of the liquid component B on a center axis of a front end portion, is fitted into the cylinder-shaped portion forming the mixing comparted chamber 1a of the powder component storing cup 1 and is provided with a convex stopper 2c, which has such a magnitude as to prevent the liquid component storing cup 2 from easily slipping into the powder component storing cup 1 at a time of pushing and breaking the second opening forming portion 2b of the liquid component storing cup 2 so as to form the circular hole for the outlet of the liquid component B and not to inhibit the liquid component storing cup 2 from entering into the powder component storing cup 1 in the case that great force is applied, on an outer side surface in the vicinity of the rear end portion. It is preferable that the liquid component storing cup 2 is constructed by a resin which does not deteriorate a characteristic of the liquid component B stored in its inner portion.

Reference numeral 3 denotes a plunger having a rod-like projection 3a including a planer peak portion (5) for pushing and breaking the second opening forming portion 2b to form the circular hole for the outlet of the liquid component storing cup 2 and the first opening forming portion 1b to form the circular hole of the powder component storing cup 1, fitted into the cylinder-shaped portion within the liquid component storing cup 2, and integrally formed by injection molding of a thermoplastic synthetic resin. It is preferable that the plunger 3 is constructed by a resin which does not deteriorate the characteristic of the liquid component B stored in the inner portion of the liquid component storing cup 2.

Reference numeral 4 denotes a nozzle having a rear end portion 4b formed in a shape corresponding to the front end portion 1c of the powder component storing cup 1, fixed to the powder component storing cup 1, and integrally formed by injection molding of a thermoplastic synthetic resin. The nozzle is provided with a protrusion portion 4c in which an inner end thereof is positioned slightly inside an outer periphery of the circular hole of the first opening forming portion 1b in such a manner as to be positioned at a position which is away from at least a hinge portion of the circular hole in the vicinity of the first opening forming portion 1b to form the circular hole for the outlet of the mixed and kneaded material of the powder component storing cup 1, on a rear end portion thereof. In other words, in the case that a plurality of protrusion portions 4c are provided on the rear end portion of the nozzle 4 in such a manner that their inner ends are positioned slightly inside the outer periphery of the circular hole of the first opening forming portion 1b, in the vicinity of the first opening forming portion 1b to form the circular hole for the outlet of the mixed and kneaded material of the powder component storing cup 1, it is sufficient that at least one of them is positioned at the position which is away from the hinge portion of the circular hole of the first opening forming portion 1b. Further, it is preferable that the front end portion 4a is tapered and curved in such a manner as to easily administer the tooth restorative material to a position to be restored of a patient.

A description will be given next of a method of using the capsule for the tooth restorative material in accordance with the present invention which is constructed by the constructing members as mentioned above.

In the capsule for the tooth restorative material in accordance with the present invention, the liquid component storing cup 2 structured such that the predetermined amount of liquid component B is stored within the liquid component storing chamber 2a and sealed by the plunger 3 is fitted to the rear end side opening portion of the powder component storing cup structured such that the fixed amount of powder component A is stored within the mixing comparted chamber 1a, the rear end portion 4b of the nozzle 4 is fixed to the outer surface of the front end portion 1c of the powder component storing cup 1, and the protrusion portion 4c in which its inner end is positioned slightly inside the outer periphery of the circular hole of the first opening forming portion 1b is provided on the rear end portion of the nozzle 4, in such a manner as to be positioned at the position which is away from at least the hinge portion of the circular hole in the vicinity of the first opening forming portion 1b to form the circular hole for the outlet of the mixed and kneaded material C of the powder component storing cup 1 (refer to FIG. 1).

Figure 2:
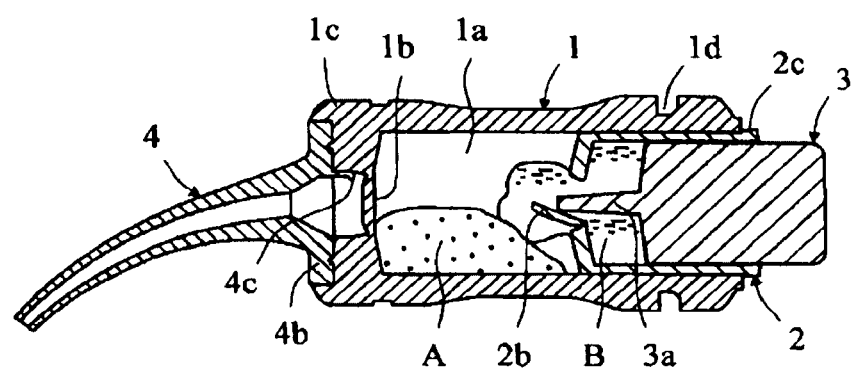
FIG. 2 is an explanatory side sectional view of a state when mixing and kneading start in the capsule for the tooth restorative material in FIG. 1.

In order to use the capsule for the tooth restorative material in accordance with the present invention under the state mentioned above, first of all, the plunger 3 fitted into the rear end side of the liquid component storing cup 2 fitted into the rear end side of the mixing and kneading chamber 1a of the powder component storing cup 1 is pressed by a finger or the like until the front end thereof comes into contact with the inner surface of the front end portion of the liquid component storing cup 2 and stops. On the basis of this operation, the second opening forming portion 2b on the center axis of the front end portion of the liquid component storing chamber 2a of the liquid component storing cup 2 is pushed and broken by the rod-like projection 3a of the plunger 3, the circular hole for the outlet is opened, and the liquid component B is completely flowed into the mixing comparted chamber 1a of the powder component storing cup 1 storing the powder component A through the circular hole for the outlet, first (refer to FIGS. 2 and 3). At this time, since the convex stopper 2c is provided on the outer side surface in the vicinity of the rear end portion of the liquid component storing cup 2, the convex stopper 2c engages with the rear end portion of the powder component storing cup 1, and the liquid component storing cup 2 does not enter into the powder component storing cup 1. In this case, when the second opening forming portion 2b of the liquid component storing cup 2 is pushed and broken by the rod-like projection 3a of the plunger 3, since the circular hole for the outlet is provided with a notch along approximately three quarters of the periphery of the circle and is formed to have a thick hinge portion at the remaining approximately one quarter, the circular hole can be easily pushed and broken, and it is possible to prevent a whole from being torn off from the liquid component storing cup 2.

Figure 3:
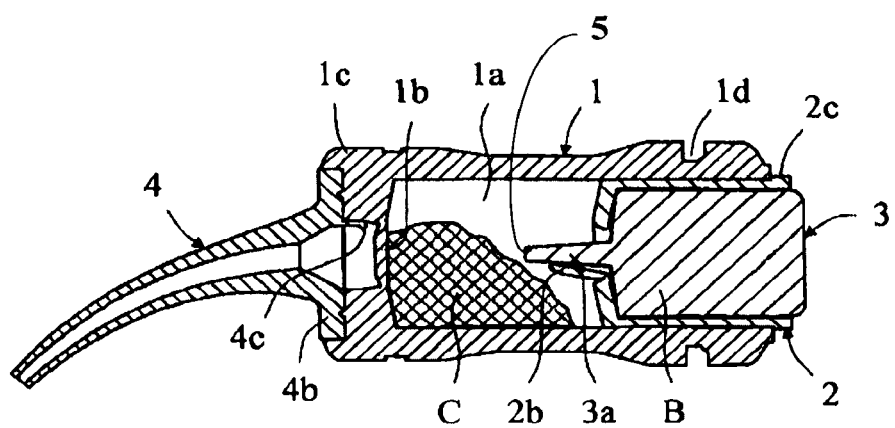
FIG. 3 is an explanatory side sectional view for showing a state after the mixing and kneading finish in the capsule for the tooth restorative material in FIG. 1.
Figure 4:
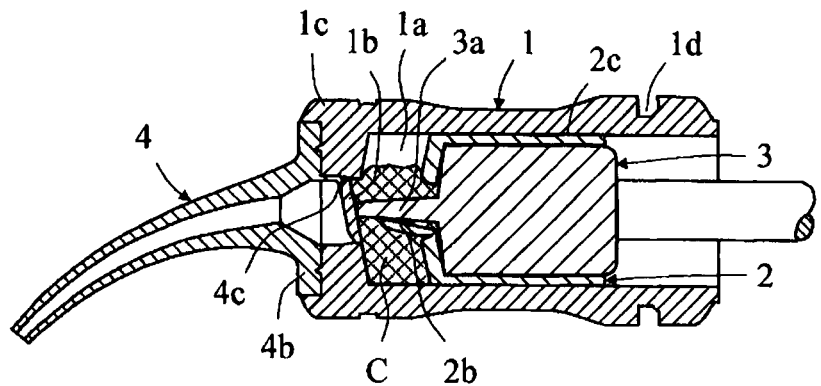
FIG. 4 is a sectional view for showing a state when pushing and breaking of a first opening forming portion of a powder component storing cup start in the capsule for the tooth restorative material in FIG. 1.
Figure 5:
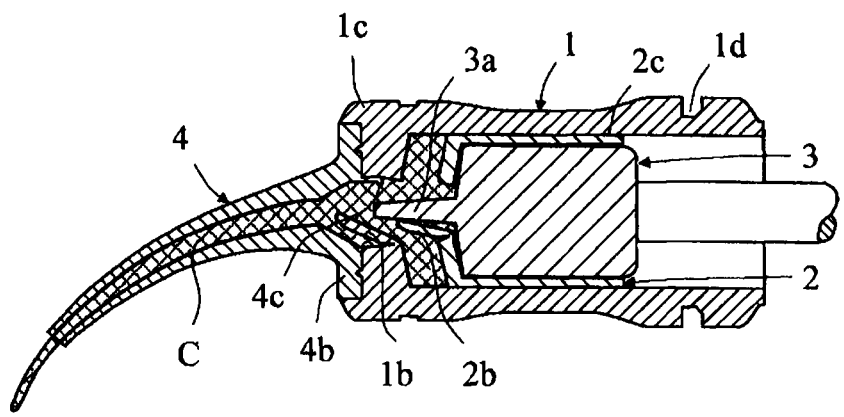
FIG. 5 is an explanatory sectional view for showing a state of extruding a mixed and kneaded material in the capsule for the tooth restorative material in FIG. 1.
Figure 6:
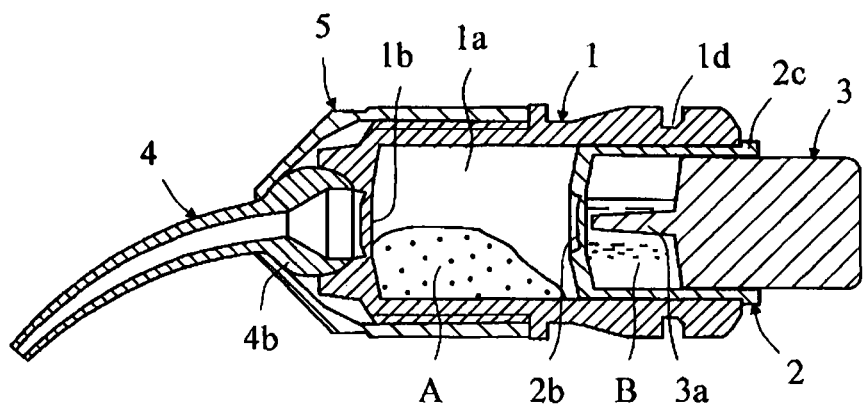
FIG. 6 is an explanatory sectional view for showing an example of a capsule for a tooth restorative material described in Japanese Patent No. 3630738.

Accordingly, after the liquid component B completely flows into the mixing comparted chamber 1a of the powder component storing cup 1 from the liquid component storing chamber 2a, the mixed and kneaded material C is obtained by mixing and kneading the powder component A and the liquid component B by installing the capsule for the tooth restorative material in accordance with the present invention to an independent exclusive mixer (refer to FIG. 3). When the mixing and kneading of the powder component A and the liquid component B are completed, a pawl (not shown) of the applier is engaged with the applier engagement groove 1d provided in the outer peripheral side surface near the rear end portion of the powder component storing cup 1, and the plunger 3 integrated with the liquid component storing cup 2 is moved toward the front end within the powder component storing cup 1 by a pressing rod of the applier. The first opening forming portion 1b on the center axis of the front end portion of the powder component storing cup 1 is pushed and broken by the rod-like projection 3a of the plunger 3 on the basis of this operation, the circular hole for the outlet is opened (refer to FIG. 4), and the mixed and kneaded material C flows into the nozzle 4 through the circular hole for the outlet (refer to FIG. 5). When the first opening forming portion 1b of the powder component storing cup 1 is pushed and broken by the rod-like projection 3a of the plunger 3, since the circular hole for the outlet is provided with a notch along approximately three quarters of the periphery of the circle and is formed to have a thick hinge portion at the remaining approximately one quarter, the circular hole can be easily pushed and broken, and it is possible to prevent a whole from being torn off from the powder component storing cup 1.

At this time, since the protrusion portion 4c in which the inner end thereof is positioned slightly inside the outer periphery of the circular hole of the first opening forming portion 1b is provided on the rear end portion of the nozzle 4, in such a manner as to be positioned at the position which is away from at least the hinge portion of the circular hole in the vicinity of the first opening forming portion 1b to form the circular hole for the outlet of the mixed and kneaded material C of the powder component storing cup 1, the protrusion portion 4c inhibits the first opening forming portion 1b of the powder component storing cup 1 from being pushed and broken in a breath. Accordingly, the phenomenon that the first opening forming portion 1b of the powder component storing cup 1 is pushed and broken in a breath and the bursting sound is thereby generated does not occur.

Accordingly, the mixed and kneaded material C is extruded from the front end portion 4a of the nozzle 4 so as to be filled in a position to be restored in a tooth, by applying the front end portion 4a of the nozzle 4 to the position to be restored in the tooth such as a cavity or the like of a patient and further moving the plunger 3 integrated with the liquid component storing cup 2 toward the front end within the powder component storing cup 1 through operation of the applier, in the state in which the first opening forming portion 1b to form the circular hole for the outlet of the mixed and kneaded material C of the powder component storing cup 1 is completely opened without generating any bursting sound. In this case, the nozzle 4 may be fixed to the powder component storing cup 1 by welding in accordance with a supersonic wave, a laser, a high-frequency wave or the like, or may be fixed by adhering with an adhesive agent, and the fixing method is not particularly limited.

What is claimed is:

1. A capsule for a tooth restorative material for directly administering a mixed and kneaded material (C) obtained by mixing and kneading the tooth restorative material constructed by two components of previously weighed fixed amounts of a powder component (A) and a liquid component (B) in an inner portion, to a position to be restored in a tooth of a patient, the capsule comprising:

a powder component storing cup (1) having a mixing comparted chamber (1a) in which the powder component (A) is stored, formed in a cylinder shape, provided with a first opening forming portion (1b) to form a circular hole for an outlet of the mixed and kneaded material (C) on a center axis of a front end portion (1c) thereof, provided with an applier engagement groove (1d) in an outer peripheral side surface near a rear end portion, and integrally formed by injection molding of a thermoplastic synthetic resin;

a liquid component storing cup (2) having a liquid component storing chamber (2a) in which the liquid component (8) is stored in an inner portion, provided with a second opening forming portion (2b) to form a circular hole for an outlet of the liquid component (8) on a center axis of a front end portion thereof, fitted into the cylinder-shaped portion forming the mixing comparted chamber (1a) of said powder component storing cup (1), provided with a convex stopper (2c) having such a magnitude as to prevent easily slipping into said powder component storing cup (1) at a time of pushing and breaking said second opening forming portion (2b) so as to form the circular hole for the outlet of the liquid component (B) and not to inhibit entering into said powder component storing cup (1) in the case that great force is applied on an outer side surface in the vicinity of the rear end portion, and integrally formed by injection molding of a thermoplastic synthetic resin;

a plunger (3) having a rod-like projection (3a) including a planer peak portion for pushing and breaking the second opening forming portion (2b) of said liquid component storing cup (2) and the first opening forming portion (1b) of said powder component storing cup (1), fitted into the cylinder-shaped portion within said liquid component storing cup (2), and integrally formed by injection molding of a thermoplastic synthetic resin; and a nozzle (4) having its rear end portion (4b) formed in a shape corresponding to the front end portion (1c) of said powder component storing cup (1), fixed to the front end portion of said powder component storing cup (1), and integrally formed by injection molding of a thermoplastic synthetic resin, wherein a protrusion portion (4c) having its inner end positioned slightly inside an outer periphery of the circular hole of the first opening forming portion (Ib) is provided on the rear end portion (4b) of said nozzle (4) in such a manner as to be positioned at a position which is in the vicinity of the first opening forming portion (1b) to form the circular hole for the outlet of the mixed and kneaded material of said powder component storing cup (1) and is away from at least a hinge portion of the circular hole.

* * * * *